(12) United States Patent
Belanoff

(10) Patent No.: US 7,361,646 B2
(45) Date of Patent: Apr. 22, 2008

(54) METHODS FOR TREATING GASTROESOPHAGEAL REFLUX DISEASE

(75) Inventor: Joseph K. Belanoff, Woodside, CA (US)

(73) Assignee: Corcept Therapeutics, Inc., Menlo Park, CA (US)

( * ) Notice: Subject to any disclaimer, the term of this patent is extended or adjusted under 35 U.S.C. 154(b) by 556 days.

(21) Appl. No.: 10/702,950

(22) Filed: Nov. 5, 2003

(65) Prior Publication Data

US 2004/0167110 A1   Aug. 26, 2004

Related U.S. Application Data

(60) Provisional application No. 60/424,199, filed on Nov. 5, 2002.

(51) Int. Cl.
*A61K 31/56* (2006.01)
*A61K 31/573* (2006.01)

(52) U.S. Cl. .................................. 514/179; 514/178
(58) Field of Classification Search ................ 514/179, 514/178

See application file for complete search history.

(56) References Cited

U.S. PATENT DOCUMENTS

| 4,753,932 | A |   | 6/1988  | Teutsch et al. |
|-----------|---|---|---------|----------------|
| 4,912,097 | A |   | 3/1990  | Teutsch et al. |
| 5,697,112 | A | * | 12/1997 | Colavito et al. ............... 5/633 |
| 6,011,025 | A |   | 1/2000  | Gebhard |
| 6,380,223 | B1|   | 4/2002  | Dow et al. |

\* cited by examiner

*Primary Examiner*—Jennifer Kim
(74) *Attorney, Agent, or Firm*—Townsend and Townsend and Crew LLP

(57) ABSTRACT

This invention relates to the discovery that agents capable of inhibiting the biological action of the glucocorticoid receptor can be used in methods for treating gastroesophageal reflux disease in a subject.

14 Claims, No Drawings

METHODS FOR TREATING GASTROESOPHAGEAL REFLUX DISEASE

CROSS REFERENCES TO RELATED APPLICATIONS

This application claims priority to U.S. 60/424,199, filed Nov. 5, 2002, which is incorporated herein by reference in its entirety.

FIELD OF THE INVENTION

This invention relates to the discovery that agents capable of inhibiting the biological action of the glucocorticoid receptor can be used in methods for reducing, eliminating, or preventing gastroesophageal reflux disease in a subject.

BACKGROUND OF THE INVENTION

Gastroesophageal reflux disease (GERD) is a chronic, relapsing condition with associated morbidity and an adverse impact on quality of life. The disease is common, with an estimated lifetime prevalence of 25 to 35 percent in the U.S. population. Psychological well-being questionnaires indicate that patients with GERD can have a poor quality of life. Indeed, the combination of symptoms, dietary restrictions, and functional limitations take their toll on an individual's sense of well-being.

In addition to the poor quality of life experienced by GERD sufferers, annual health care costs related to this disease are high. Individuals who suffer from GERD are prone to complications such as severe esophagitis, recurrent esophageal strictures, severe pulmonary symptoms, and Barrett's esophagus, which carries with it an increased risk for the development of adenocarcinoma of the esophagus.

Antacids remain the drugs of choice for quick relief of symptoms associated with GERD. These agents act primarily by rapidly increasing the pH of the gastric refluxate. Although antacids are effective in relieving symptoms, they cannot be used as sole agents for achieving esophageal healing because of the high dosage requirements and consequent lack of patient compliance.

Over-the-Counter $H_2$-Receptor Blockers may also be prescribed for the treatment and prevention of GERD. These agents are indicated for the prevention and relief of heartburn, acid indigestion and sour stomach. They do not act as rapidly as antacids, but they provide longer relief of symptoms. Unfortunately, standard dosages of these agents do not completely inhibit acid secretion, and so do not typically promote esophageal healing.

Clearly, there is a need in the art for a safe and effective GERD treatment that will reduce and/or eliminate the causes and/or symptoms of GERD. The ideal treatment would also promote healing of damaged esophageal tissues, thereby reducing health cost associated with the disease. Fortunately, the current invention addresses these and other needs. The invention is based, at least in part, on the surprising discovery that glucocorticoid receptor antagonists are effective agents for the treatment of GERD.

Corticosteroids are steroid hormones released by the adrenal glands. The most significant human adrenal corticosteroids are cortisol, corticosterone and aldosterone. Corticosteroids produce cellular effects following binding to receptors located in the cytoplasm of the cell. Two general classes of corticosteroid receptors are now recognized, the mineralocorticoid receptors (also termed type I, or MR) and the glucocorticoid receptors (also termed type II, or GR).

Mineralocorticoid receptors (MRs) bind cortisol with ten-fold higher affinity than glucocorticoid receptors (GRs) bind glucocorticoids. Thus, the activation of the two classes of receptors may differ depending on the corticosteroid (cortisol) concentration. Blood levels of the glucocorticoid cortisol vary over a wide range during the day. In general, normal cortisol concentrations in the blood range from about 0.5 nM to about 50 nM; however, in response to stress, cortisol concentration may exceed 100 nM.

Glucocorticoid blockers are agents that block or reduce the effects of glucocorticoids. Such interference with glucocorticoid action may, for example, be due to interference with binding of glucocorticoid agonists to glucocorticoid receptors (GR), or to interference with the action of agonist-bound GR at the cell nucleus, or to interference with expression or processing of gene products induced by the action of agonist-bound GR at the nucleus. Glucocorticoid receptor antagonists (GR antagonists) are compounds which inhibit the effect of the native ligand or of glucocorticoid agonists on GR. One mode of action of GR antagonists is to inhibit the binding of GR ligands to GR. A discussion of glucocorticoid antagonists may be found in Agarwal et al. "Glucocorticoid antagonists", FEBS Lett., 217:221-226 (1987). An example of a GR antagonist is mifepristone, (11β,17β) 11[4(dimethylamino)phenyl]-17hydroxy-17(1 propynyl)estra-4,9dien-3one, also known as RU-486 or RU-38486. See U.S. Pat. No. 4,368,085. Mifepristone binds specifically to GR with an affinity about 18 times that of the affinity of cortisol for GR. GR antagonists may be steroids, such as mifepristone, or non-steroids.

The present inventors have determined for the first time that glucocorticoid receptor antagonists are effective agents for the treatment of gastroesophageal reflux disease. Thus, the present invention fulfills the need for an effective method for the treatment of gastroesophageal reflux disease by providing methods of administering glucocorticoid receptor antagonists to a subject.

BRIEF SUMMARY OF THE INVENTION

The present invention is based at least in part, upon the discovery that administration of a glucocorticoid receptor antagonist provides an effective and improved treatment for gastroesophageal reflux disease. Thus, in one aspect, the invention is directed toward methods of treating gastroesophageal reflux disease in a subject, provided that the subject is not otherwise in need of treatment with a glucocorticoid receptor antagonist.

In one aspect of the invention, the glucocorticoid receptor antagonist comprises a steroidal skeleton with at least one phenyl-containing moiety in the 11-beta position of the steroidal skeleton. In one aspect, the phenyl-containing moiety in the 11-beta position of the steroidal skeleton is a dimethylaminophenyl moiety. In another aspect, the glucocorticoid receptor antagonist is mifepristone.

In one aspect of the present invention, the glucocorticoid receptor antagonist is selected from the group consisting of 11β-(4-dimethylaminoethoxyphenyl)-17α-propynyl-17β-hydroxy-4,9-estradien-3-one and 17β-hydroxy-17α-19-(4-methylphenyl)androsta-4,9(11)-dien-3-one. In another aspect, the glucocorticoid receptor antagonist is selected from the group consisting 4α(S)-Benzyl-2(R)-prop-1-ynyl-1,2,3,4,4α,9,10,10α(R)-octahydro-phenanthrene-2,7-diol and 4α(S)-Benzyl-2(R)-chloroethynyl-1,2,3,4,4α,9,10,10α(R)-octahydro-phenanthrene-2,7-diol.

In another one aspect, the glucocorticoid receptor antagonist is (11β,17β)-11-(1,3-benzodioxol-5-yl)-17-hydroxy-17-(1-propynyl)estra-4,9-dien-3-one.

In another aspect of the present invention, the glucocorticoid receptor antagonist is administered in a daily amount of between about 0.5 to about 35 mg per kilogram of body weight per day. In another aspect, the glucocorticoid receptor antagonist is administered in a daily amount of between about 5 to about 15 mg per kilogram of body weight per day.

In one aspect of the present invention, the administration is once per day. In yet another aspect, the mode of administration is by a transdermal application, by a nebulized suspension, or by an aerosol spray. In another aspect, the mode of administration is oral.

In another aspect the invention also provides a kit for treating gastroesophageal reflux disease in a subject. The kit comprises a specific glucocorticoid receptor antagonist and an instructional material teaching the indications, dosage and schedule of administration of the glucocorticoid receptor antagonist to a patient suffering from gastroesophageal reflux disease.

DETAILED DESCRIPTION OF THE INVENTION

Definitions

The term "gastroesophageal reflux disease" or "GERD" refers to a condition resulting from food or liquid traveling from the stomach back up into the esophagus. This partially digested material is usually acidic and can irritate the esophagus, often causing heartburn and other symptoms. GERD can be associated with a number of conditions, including, but not limited to incompetent esophageal sphincters, hiatal hernia, obesity, recurrent or persistent vomiting, previous esophageal surgery or esophageal stricture The term "prophylactic" refers to an agent that acts to prevent disease, such as gastroesophageal reflux disease. In one aspect, a glucocorticoid receptor antagonist of the invention is administered prophylactically to prevent the onset or recurrence of gastroesophageal reflux disease.

The terms "treating", "treatment", "to treat" refer to means for reducing or eliminating gastroesophageal reflux disease and or the accompanying symptoms in a subject. Treatment refers to any indicia of success in reduction, elimination, or amelioration of gastroesophageal reflux, including any objective or subjective parameter such as abatement; remission; diminishing of symptoms, or lessening of symptoms or making the condition more tolerable to the subject; rendering the refluxate harmless, improving esophageal clearance, protecting the esophageal mucosa; or improving a patient's physical or mental well-being. For example, success of treatment by methods of the invention could be measured by comparing the severity of gastroesophageal reflux and the nature of the refluxant in the year before treatment with anti-glucocorticoids of the invention was initiated, with the year following the initiation of treatment. The treatment or amelioration of symptoms can be based on objective or subjective parameters; including the results of a physical examination, or any other appropriate means known in the art.

The term "cortisol" refers to a family of compositions also referred to as hydrocortisone, and any synthetic or natural analogues thereof.

The term "glucocorticoid receptor" ("GR") refers to a family of intracellular receptors also referred to as the cortisol receptor, which specifically bind to cortisol and/or cortisol analogs. The term includes isoforms of GR, recombinant GR and mutated GR.

The term "mifepristone" refers to a family of compositions also referred to as RU486, or RU38.486, or 17-β-hydroxy-11-β-(4-dimethyl-aminophenyl)-17-α-(1-propynyl)-estra-4,9-dien-3-one), or 11-β-(4dimethylaminophenyl)-17-β-hydroxy-17-α-(1-propynyl)-estra-4,9-dien-3-one), or analogs thereof, which bind to the GR, typically with high affinity, and inhibit the biological effects initiated/mediated by the binding of any cortisol or cortisol analogue to a GR receptor. Chemical names for RU-486 vary; for example, RU486 has also been termed: 11β-[p-(Dimethylamino)phenyl]-17β-hydroxy-17-(1-propynyl)-estra-4,9-dien-3-one; 11β-(4-dimethyl-aminophenyl)-17β-hydroxy-17α-(prop-1-ynyl)-estra-4,9-dien-3-one; 17β-hydroxy-11β-(4-dimethylaminophenyl-1)-17α-(propynyl-1)-estra-4,9-diene-3-one; 17β-hydroxy-11β-(4-dimethylaminophenyl-1)-17α-(propynyl-1)-E; (11β,17β)-11-[4-dimethylamino)-phenyl]-17-hydroxy-17-(1-propynyl)estra-4,9-dien-3-one; and 11β-[4-(N,N-dimethylamino)phenyl]-17α-(prop-1-ynyl)-D-4,9-estradiene-17β-ol-3-one.

The term "specific glucocorticoid receptor antagonist" refers to any composition or compound which partially or completely inhibits (antagonizes) the binding of a glucocorticoid receptor (GR) agonist, such as cortisol, or cortisol analogs, synthetic or natural, to a GR. By "specific", we intend the drug to preferentially bind to the GR rather than the mineralocorticoid receptor (MR) with an affinity at least 100-fold, and frequently 1000-fold.

A subject "not otherwise in need of treatment with a glucocorticoid receptor antagonist" is an individual or patient who is not being treated with antiglucocorticoid compounds for any disorder accepted by the medical community to be effectively treatable with antiglucocorticoid compounds. Conditions known in the art and accepted by the medical community to be effectively treatable with glucocorticoid receptor antagonists include: Cushing's disease, drug withdrawal, dementia, stress disorders, anxiety disorders (U.S. Pat. No. 5,741,787), depression, psychotic major depression (U.S. Pat. No. 6,150,349), schizoaffective disorder, diabetes, rheumatoid arthritis, autoimmune disease, HIV infection, dermatitis, inflammation, fibromyalgia, central nervous system disease, neurodegeneration, neural injuries, pelvic pain, and various cancers.

I. Introduction

This invention pertains to the surprising discovery that agents that can inhibit glucocorticoid-induced biological responses are effective for treating gastroesophageal reflux disease. In treating gastroesophageal reflux disease, the methods of the invention can ameliorate, eliminate, reduce or prevent the symptoms of gastroesophageal reflux disease. In one embodiment, the methods of the invention use agents that act as GR antagonists, blocking the interaction of cortisol with GR, to treat gastroesophageal reflux disease. The methods of the invention are effective in treating gastroesophageal reflux disease in an afflicted patient.

Cortisol acts by binding to an intracellular, glucocorticoid receptor (GR). In humans, glucocorticoid receptors are present in two forms: a ligand-binding GR-alpha of 777 amino acids; and, a GR-beta isoform that differs in only the last fifteen amino acids. The two types of GR have high affinity for their specific ligands, and are considered to function through the same signal transduction pathways.

The biological effects of cortisol, including pathologies or dysfunctions caused by hypercortisolemia, can be modulated and controlled at the GR level using receptor antagonists. Several different classes of agents are able to act as GR antagonists, i.e., to block the physiologic effects of GR-agonist binding (the natural agonist is cortisol). These antagonists include compositions, which, by binding to GR, block the ability of an agonist to effectively bind to and/or activate the GR. One family of known GR antagonists, mifepristone and related compounds, are effective and potent anti-glucocorticoid agents in humans (Bertagna, *J. Clin. Endocrinol. Metab.* 59:25, 1984). Mifepristone binds to the GR with high affinity, with a K of dissociation <$10^{-9}$ M (Cadepond, *Annu. Rev. Med.* 48:129, 1997). Thus, in one embodiment of the invention, mifepristone and related compounds are used to treat gastroesophageal reflux disease in a subject.

As the methods of the invention include use of any means to inhibit the biological effects of an agonist-bound GR, illustrative compounds and compositions which can be used to treat gastroesophageal reflux disease in a subject are also set forth. Routine procedures that can be used to identify further compounds and compositions able to block the biological response caused by a GR-agonist interaction for use in practicing the methods of the invention are also described. As the invention provides for administering these compounds and compositions as pharmaceuticals, routine means to determine GR antagonist drug regimens and formulations to practice the methods of the invention are set forth below.

II. Diagnosis of Gastroesophageal Reflux Disease in a Subject

Gastroesophageal reflux disease (GERD) is characterized by heartburn and regurgitation, which may also include dysphagia. The heartburn characteristic of GERD is most frequently described as a sub-sternal burning that occurs after meals and often worsens when lying down. Other symptoms that may be associated with GERD include, but are not limited to atypical chest pain, hoarseness, nausea, cough, odynophagia and asthma.

Diagnosis may be made from the presentation of the characteristic GERD symptoms alone, but sometimes further tests are needed to confirm the diagnosis of GERD. In cases wher further diagnosis is warranted, the further diagnosis is typically made by treating patients with medications that suppress the production of acid by the stomach. Acid suppressing medications include proton pump inhibitors such as Prilosec (omeprazole), Prevacid (lansoprazole), Aciphex (rabeprazole), Protonix (pantoprazole), and Nexium (esomeprazole), and histamine blockers such as Zantac (ranitidine), Tagamet (cimetidine), and Pepcid (famotidine). If the heartburn then is diminished to a large extent, a diagnosis of GERD may be confirmed.

In some cases further diagnostic measures may be carried out. For example, if doubts remain about the diagnosis the after the above tests are completed, or if complications are a concern. The gold standard for diagnosing GERD is esophageal acid testing.

Patients with the symptoms or complications of GERD have reflux of more acid, and the acid remains longer in the esophagus when compared to healthy individuals. Thus, diagnosis of GERD can be confirmed or extended by performing a 24-hour esophageal pH test. A pH monitor is placed in the esophagus above the lower esophageal sphincter, and the pH is recorded at regular intervals over a 24-hour test period. Combined with a diary of symptoms kept by the patient, this method permits GERD to be diagnosed and correlated with the lowering of esophageal pH that occurs with reflux.

A method for prolonged measurement (48 hours) of acid exposure in the esophagus may also be conducted. The method utilizes a small, wireless capsule that is attached to the esophagus just above the LES. The capsule measures the acid refluxing into the esophagus and transmits this information to a receiver that is worn at the waist. At the completion of the test, the information from the receiver is downloaded into a computer and analyzed. The capsule falls off of the esophagus after 3-5 days and is passed in the stool.

III. General Laboratory Procedures

When practicing the methods of the invention, a number of general laboratory tests can be used to assist in the diagnosis, progress and prognosis of the patient with gastroesophageal reflux disease, including monitoring of parameters such as blood cortisol, drug metabolism, brain structure and function and the like. These procedures can be helpful because all patients metabolize and react to drugs uniquely. In addition, such monitoring may be important because each GR antagonist has different pharmacokinetics. Different patients and disease conditions may require different dosage regimens and formulations. Such procedures and means to determine dosage regimens and formulations are well described in the scientific and patent literature. A few illustrative examples are set forth below.

a. Determining Blood Cortisol Levels

The invention may be practiced upon patients with apparently normal levels of blood cortisol. However, since the treatment for gastroesophageal reflux disease comprises administration of a glucocorticoid receptor antagonist, monitoring blood cortisol and determining baseline cortisol levels are useful laboratory tests to aid in the diagnosis, treatment and prognosis of a gastroesophageal reflux disease patient. A wide variety of laboratory tests exist that can be used to determine whether an individual is normal, hypo- or hypercortisolemic. Patients with gastroesophageal reflux disease typically have normal levels of cortisol that are often less than 25 µg/dl in the morning, and frequently about 15 µg/dl or less in the afternoon, although the values often fall at the high end of the normal range, which is generally considered to be 5-15 µg/dl in the afternoon.

Immunoassays such as radioimmunoassays are commonly used because they are accurate, easy to do and relatively cheap. Because levels of circulating cortisol are an indicator of adrenocortical function, a variety of stimulation and suppression tests, such as ACTH Stimulation, ACTH Reserve, or dexamethasone suppression (see, e.g., Greenwald, *Am. J. Psychiatry* 143:442-446, 1986), can also provide diagnostic, prognostic or other information to be used adjunctively in the methods of the invention.

One such assay available in kit form is the radioimmunoassay available as "Double Antibody Cortisol Kit" (Diagnostic Products Corporation, Los Angeles, Calif.), (*Acta Psychiatr. Scand.* 70:239-247, 1984). This test is a competitive radioimmunoassay in which $^{125}$I-labeled cortisol competes with cortisol from an clinical sample for antibody sites. In this test, due to the specificity of the antibody and lack of any significant protein effect, serum and plasma samples require neither preextraction nor predilution. This assay is described in further detail in Example 2, below.

b. Determination of Blood/Urine Mifepristone Levels

Because a patient's metabolism, clearance rate, toxicity levels, etc. differs with variations in underlying primary or secondary disease conditions, drug history, age, general medical condition and the like, it may be necessary to measure blood and urine levels of GR antagonist. Means for such monitoring are well described in the scientific and patent literature. As in one embodiment of the invention mifepristone is administered to treat gastroesophageal reflux disease, an illustrative example of determining blood and urine mifepristone levels is set forth in the Example below.

c. Other Laboratory Procedures

Laboratory tests monitoring and measuring GR antagonist metabolite generation, plasma concentrations and clearance rates, including urine concentration of antagonist and metabolites, may also be useful in practicing the methods of the invention. For example, mifepristone has two hydrophilic, N-monomethylated and N-dimethylated, metabolites. Plasma and urine concentrations of these metabolites (in addition to RU486) can be determined using, for example, thin layer chromatography, as described in Kawai *Pharmacol. and Experimental Therapeutics* 241:401-406, 1987.

IV. Glucocorticoid Receptor Antagonists to Treat Gastroesophageal Reflux Disease in a Subject The invention provides for methods for treating gastroesophageal reflux disease in a subject utilizing any composition or compound that can block a biological response associated with the binding of cortisol or a cortisol analogue to a GR. Antagonists of GR activity utilized in the methods of the invention are well described in the scientific and patent literature. A few illustrative examples are set forth below.

A. Steroidal Anti-Glucocorticoids as GR Antagonists.

Steroidal glucocorticoid antagonists are administered to treat gastroesophageal reflux disease in various embodiments of the invention. Steroidal antiglucocorticoids can be obtained by modification of the basic structure of glucocorticoid agonists, i.e., varied forms of the steroid backbone. The structure of cortisol can be modified in a variety of ways. The two most commonly known classes of structural modifications of the cortisol steroid backbone to create glucocorticoid antagonists include modifications of the 11-beta hydroxy group and modification of the 17-beta side chain (see, e.g., Lefebvre, *J. Steroid Biochem.* 33:557-563, 1989).

Examples of steroidal GR antagonists include androgentype steroid compounds as described in U.S. Pat. No. 5,929,058, and the compounds disclosed in U.S. Pat. Nos. 4,296,206; 4,386,085; 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; 5,616,458, 5,696,127, and 6,303,591. Such steroidal GR antagonists include cortexolone, dexamethasone-oxetanone, 19-nordeoxycorticosterone, 19-norprogesterone, cortisol-21-mesylate; dexamethasone-21-mesylate, 11β-(4-dimethylaminoethoxyphenyl)-17α-propynyl-17β-hydroxy-4,9-estradien-3-one (RU009), and 17β-hydroxy-17α-19-(4-methylphenyl)androsta-4,9 (11)-dien-3-one (RU044).

Other examples of steroidal antiglucocorticoids are disclosed in Van Kampen et al. (2002) Eur. J. Pharmacol. 457(2-3):207, WO 03/043640, EP 0 683 172 B1, and EP 0 763 541 B1, each of which is incorporated herein by reference. EP 0 763 541 B1 and Hoyberg et al., *Int'l J. of Neuro-psychopharmacology*, 5:Supp. 1, S148 (2002); disclose the compound (11β,17β)-11-(1,3-benzodioxol-5-yl)-17-hydroxy-17-(1-propynyl)estra-4,9-dien-3-one (ORG 34517) which in one embodiment, is administered in an amount effective to treat gastroesophageal reflux disease in a subject.

1. Removal or Substitution of the 11-beta Hydroxy Group

Glucocorticoid antagonists with modified steroidal backbones comprising removal or substitution of the 11-beta hydroxy group are administered in one embodiment of the invention. This class includes natural antiglucocorticoids, including cortexolone, progesterone and testosterone derivatives, and synthetic compositions, such as mifepristone (Lefebvre, et al. supra). Preferred embodiments of the invention include all 11-beta-aryl steroid backbone derivatives because these compounds are devoid of progesterone receptor (PR) binding activity (Agarwal, FEBS 217:221-226, 1987). Another preferred embodiment comprises an 11-beta phenyl-aminodimethyl steroid backbone derivative, i.e., mifepristone, which is both an effective anti-glucocorticoid and anti-progesterone agent. These compositions act as reversibly-binding steroid receptor antagonists. For example, when bound to a 11-beta phenyl-aminodimethyl steroid, the steroid receptor is maintained in a conformation that cannot bind its natural ligand, such as cortisol in the case of GR (Cadepond, 1997, supra).

Synthetic 11-beta phenyl-aminodimethyl steroids include mifepristone, also known as RU486, or 17-beta-hydrox-11-beta-(4-dimethyl-aminophenyl)17-alpha-(1-propynyl)estra-4,9-dien-3-one). Mifepristone has been shown to be a powerful antagonist of both the progesterone and glucocorticoid (GR) receptors. Another 11-beta phenyl-aminodimethyl steroids shown to have GR antagonist effects includes RU009 (RU39.009), 11-beta-(4-dimethyl-aminoethoxyphenyl)-17-alpha-(propynyl-17-beta-hydroxy-4,9-estradien-3-one) (see Bocquel, J. Steroid Biochem. Molec. Biol. 45:205-215, 1993). Another GR antagonist related to RU486 is RU044 (RU43.044) 17-beta-hydrox-17-alpha-19-(4-methyl-phenyl)-androsta-4,9(11)-dien-3-one) (Bocquel, 1993, supra). See also Teutsch, Steroids 38:651-665, 1981; U.S. Pat. Nos. 4,386,085 and 4,912,097.

One embodiment includes compositions containing the basic glucocorticoid steroid structure which are irreversible anti-glucocorticoids. Such compounds include alpha-ketomethanesulfonate derivatives of cortisol, including cortisol-21-mesylate (4-pregnene-11-beta, 17-alpha, 21-triol-3, 20-dione-21-methane-sulfonate and dexamethasone-21-mesylate (16-methyl-9alpha-fluoro-1,4-pregnadiene-11 beta, 17-alpha, 21-triol-3, 20-dione-21-methane-sulfonte). See Simons, *J. Steroid Biochem.* 24:25-32, 1986; Mercier, *J. Steroid Biochem.* 25:11-20, 1986; U.S. Pat. No. 4,296,206.

2. Modification of the 17-beta Side Chain Group

Steroidal antiglucocorticoids which can be obtained by various structural modifications of the 17-beta side chain are also used in the methods of the invention. This class includes synthetic antiglucocorticoids such as dexamethasone-oxetanone, various 17, 21-acetonide derivatives and 17-beta-carboxamide derivatives of dexamethasone (Lefebvre, 1989, supra; Rousseau, *Nature* 279:158-160, 1979).

3. Other Steroid Backbone Modifications

GR antagonists used in the various embodiments of the invention include any steroid backbone modification which effects a biological response resulting from a GR-agonist interaction. Steroid backbone antagonists can be any natural or synthetic variation of cortisol, such as adrenal steroids missing the C-19 methyl group, such as 19-nordeoxycorticosterone and 19-norprogesterone (Wynne, Endocrinology 107:1278-1280, 1980).

In general, the 11-beta side chain substituent, and particularly the size of that substituent, can play a key role in determining the extent of a steroid's antiglucocorticoid activity. Substitutions in the A ring of the steroid backbone can also be important. 17-hydroxypropenyl side chains generally decrease antiglucocorticoid activity in comparison to 17-propinyl side chain containing compounds.

Additional glucocorticoid receptor antagonists known in the art and suitable for practice of the invention include 21-hydroxy-6,19-oxidoprogesterone (see Vicent, Mol. Pharm. 52:749-753, 1997), Org31710 (see Mizutani, *J Steroid Biochem Mol Biol* 42(7):695-704, 1992), RU43044, RU40555 (see Kim, *J Steroid Biochem Mol Biol.* 67(3):213-22, 1998), RU28362, and ZK98299.

B. Non-Steroidal Anti-Glucocorticoids as Antagonists.

Non-steroidal glucocorticoid antagonists are also used in the methods of the invention to gastroesophageal reflux disease in a subject. These include synthetic mimetics and analogs of proteins, including partially peptidic, pseudopeptidic and non-peptidic molecular entities. For example, oligomeric peptidomimetics useful in the invention include (alpha-beta-unsaturated) peptidosulfonamides, N-substituted glycine derivatives, oligo carbamates, oligo urea peptidomimetics, hydrazinopeptides, oligosulfones and the like (see, e.g., Amour, *Int. J. Pept. Protein Res.* 43:297-304, 1994; de Bont, *Bioorganic & Medicinal Chem.* 4:667-672, 1996). The creation and simultaneous screening of large libraries of synthetic molecules can be carried out using well-known techniques in combinatorial chemistry, for example, see van Breemen, *Anal Chem* 69:2159-2164, 1997; and Lam, *Anticancer Drug Des* 12:145-167, 1997. Design of peptidomimetics specific for GR can be designed using computer programs in conjunction with combinatorial chemistry (combinatorial library) screening approaches (Murray, *J. of Computer-Aided Molec. Design* 9:381-395, 1995; Bohm, *J. of Computer-Aided Molec. Design* 10:265-272, 1996). Such "rational drug design" can help develop peptide isomerics and conformers including cycloisomers, retro-inverso isomers, retro isomers and the like (as discussed in Chorev, *TibTech* 13:438-445, 1995).

Examples of non-steroidal GR antagonists include ketoconazole, clotrimazole; N-(triphenylmethyl)imidazole; N-([2-fluoro-9-phenyl]fluorenyl)imidazole; N-([2-pyridyl]diphenylmethyl)imidazole; N-(2-[4,4',4"-trichlorotrityl]oxyethyl)morpholine; 1-(2[4,4',4"-trichlorotrityl]oxyethyl)-4-(2-hydroxyethyl)piperazine dimaleate; N-([4,4',4"]-trichlorotrityl)imidazole; 9-(3-mercapto-1,2,4-triazolyl)-9-phenyl-2,7-difluorofluorenone; 1-(2-chlorotrityl)-3,5-dimethylpyrazole; 4-(morpholinomethyl)-A-(2-pyridyl)benzhydrol; 5-(5-methoxy-2-(N-methylcarbamoyl)-phenyl)dibenzosuberol; N-(2-chlorotrityl)-L-prolinol acetate; 1-(2-chlorotrityl)-2-methylimidazole; 1-(2-chlorotrityl)-1,2,4-triazole; 1,S-bis(4,4',4"-trichlorotrityl)-1,2,4-triazole-3-thiol; and N-((2,6-dichloro-3-methylphenyl)diphenyl)methylimidazole (see U.S. Pat. No. 6,051,573); the GR antagonist compounds disclosed in U.S. Pat. Nos. 5,696,127 and 6,570,020; the GR antagonist compounds disclosed in US Patent Application 20020077356, the glucocorticoid receptor antagonists disclosed in Bradley et al., *J. Med. Chem.* 45, 2417-2424 (2002), e.g., 4α(S)-Benzyl-2(R)-chloroethynyl-1,2,3,4,4α,9,10,10α(R)-octahydro-phenanthrene-2,7-diol ("CP 394531") and 4α(S)-Benzyl-2(R)-prop-1-ynyl-1,2,3,4,4α,9,10,10α(R)-octahydro-phenanthrene-2,7-diol ("CP 409069") the compounds disclosed in PCT International Application No. WO 96/19458, which describes non-steroidal compounds which are high-affinity, highly selective antagonists for steroid receptors, such as 6-substituted-1,2-dihydro-N-protected-quinolines; and some κ opioid ligands, such as the κ opioid compounds dynorphin-1,13-diamide, U50,488 (trans-(1R,2R)-3,4-dichloro-N-methyl-N-[2-(1-pyrrolidinyl)cyclohexyl]benzeneacetamide), bremazocine and ethylketocyclazocine; and the non-specific opioid receptor ligand, naloxone, as disclosed in Evans et al., *Endocrin.,* 141:2294-2300 (2000).

C. Identifying Specific Glucocorticoid Receptor Antagonists

Because any specific GR antagonist can be used to treat gastroesophageal reflux disease in a subject, in addition to the compounds and compositions described above, additional useful GR antagonists can be determined by the skilled artisan. A variety of such routine, well-known methods can be used and are described in the scientific and patent literature. They include in vitro and in vivo assays for the identification of additional GR antagonists. A few illustrative examples are described below.

One assay that can be used to identify a GR antagonist of the invention measures the effect of a putative GR antagonist on tyrosine amino-transferase activity in accordance with the method of Granner, Meth. Enzymol. 15:633, 1970. This analysis is based on measurement of the activity of the liver enzyme tyrosine amino-transferase (TAT) in cultures of rat hepatoma cells (RHC). TAT catalyzes the first step in the metabolism of tyrosine and is induced by glucocorticoids (cortisol) both in liver and hepatoma cells. This activity is easily measured in cell extracts. TAT converts the amino group of tyrosine to 2-oxoglutaric acid. P-hydroxyphenylpyruvate is also formed. It can be converted to the more stable p- hydoxybenzaldehyde in an alkaline solution and quantitated by absorbance at 331 nm. The putative GR antagonist is co-administered with cortisol to whole liver, in vivo or ex vivo, or hepatoma cells or cell extracts. A compound is identified as a GR antagonist when its administration decreases the amount of induced TAT activity, as compared to control (i.e., only cortisol or GR agonist added) (see also Shirwany, Biochem. Biophys. Acta 886:162-168, 1986).

Further illustrative of the many assays which can be used to identify compositions utilized in the methods of the invention, in addition to the TAT assay, are assays based on glucocorticoid activities in vivo. For example, assays that assess the ability of a putative GR antagonist to inhibit uptake of 3H-thymidine into DNA in cells which are stimulated by glucocorticoids can be used. Alternatively, the putative GR antagonist can complete with 3H-dexamethasone for binding to a hepatoma tissue culture GR (see, e.g., Choi, et al., Steroids 57:313-318, 1992). As another example, the ability of a putative GR antagonist to block nuclear binding of 3H-dexamethasone-GR complex can be used (Alexandrova et al., J. Steroid Biochem. Mol. Biol. 41:723-725, 1992). To further identify putative GR antagonists, kinetic assays able to discriminate between glucocorticoid agonists and antagonists by means of receptor-binding kinetics can also be used (as described in Jones, Biochem J. 204:721-729, 1982).

In another illustrative example, the assay described by Daune, Molec. Pharm. 13:948-955, 1977; and in U.S. Pat. No. 4,386,085, can be used to identify anti-glucocorticoid activity. Briefly, the thymocytes of adrenalectomized rats are incubated in nutritive medium containing dexamethasone with the test compound (the putative GR antagonist) at varying concentrations. 3H-uridine is added to the cell culture, which is further incubated, and the extent of incorporation of radiolabel into polynucleotide is measured.

Glucocorticoid agonists decrease the amount of 3H-uridine incorporated. Thus, a GR antagonist will oppose this effect.

For additional compounds that can be utilized in the methods of the invention and methods of identifying and making such compounds, see U.S. Pat. No.: 4,296,206 (see above); U.S. Pat. No. 4,386,085 (see above); U.S. Pat. Nos. 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; and 5,616,458; and WO 96/19458, which describes non-steroidal compounds which are high-affinity, highly selective modulators (antagonists) for steroid receptors, such as 6-substituted-1,2-dihydro N-1 protected quinolines.

The specificity of the antagonist for the GR relative to the MR can be measured using a variety of assays known to those of skill in the art. For example, specific antagonists can be identified by measuring the ability of the antagonist to bind to the GR compared to the MR (see, e.g., U.S. Pat. Nos. 5,606,021; 5,696,127; 5,215,916; 5,071,773). Such an analysis can be performed using either direct binding assay or by assessing competitive binding to the purified GR or MR in the presence of a known antagonist. In an exemplary assay, cells that are stably expressing the glucocorticoid receptor or mineralocorticoid receptor (see, e.g., U.S. Pat. No. 5,606,021) at high levels are used as a source of purified receptor. The affinity of the antagonist for the receptor is then directly measured. Those antagonists that exhibit at least a 100-fold higher affinity, often 1000-fold, for the GR relative to the MR are then selected for use in the methods of the invention.

A GR-specific antagonist may also be defined as a compound that has the ability to inhibit GR-mediated activities, but not MR-mediated activities. One method of identifying such a GR-specific antagonist is to assess the ability of an antagonist to prevent activation of reporter constructs using transfection assays (see, e.g., Bocquel et al, J. Steroid Biochem Molec. Biol. 45:205-215, 1993; U.S. Pat. Nos. 5,606,021, 5,929,058). In an exemplary transfection assay, an expression plasmid encoding the receptor and a reporter plasmid containing a reporter gene linked to receptor-specific regulatory elements are cotransfected into suitable receptor-negative host cells. The transfected host cells are then cultured in the presence and absence of a hormone, such as cortisol or analog thereof, able to activate the hormone responsive promoter/enhancer element of the reporter plasmid. Next the transfected and cultured host cells are monitored for induction (i.e., the presence) of the product of the reporter gene sequence. Finally, the expression and/or steroid binding-capacity of the hormone receptor protein (coded for by the receptor DNA sequence on the expression plasmid and produced in the transfected and cultured host cells), is measured by determining the activity of the reporter gene in the presence and absence of an antagonist. The antagonist activity of a compound may be determined in comparison to known antagonists of the GR and MR receptors (see, e.g., U.S. Pat. No. 5,696,127). Efficacy is then reported as the percent maximal response observed for each compound relative to a reference antagonist compound. A GR-specific antagonist is considered to exhibit at least a 100-fold, often 1000-fold or greater, activity towards the GR relative to the MR.

V. Treating Gastroesophageal Reflux Disease in a Subject Using Glucocorticoid Receptor Antagonists Antiglucocorticoids, such as mifepristone, are formulated as pharmaceuticals to be used in the methods of the invention to treat gastroesophageal reflux disease in a subject. Any composition or compound that can block a biological response associated with the binding of cortisol or a cortisol analogue to a GR can be used as a pharmaceutical in the invention. Routine means to determine GR antagonist drug regimens and formulations to practice the methods of the invention are well described in the patent and scientific literature, and some illustrative examples are set forth below.

A. Glucocorticoid Receptor Antagonists as Pharmaceutical Compositions

The GR antagonists used in the methods of the invention can be administered by any means known in the art, e.g., parenterally, topically, orally, or by local administration, such as by aerosol or transdermally. The methods of the invention provide for therapeutic treatments. The GR antagonists as pharmaceutical formulations can be administered in a variety of unit dosage forms depending upon whether the gastroesophageal reflux disease is being treated during an attack, the general medical condition of each patient, the resulting preferred method of administration and the like. Details on techniques for formulation and administration are well described in the scientific and patent literature, see, e.g., the latest edition of Remington's Pharmaceutical Sciences, Mack Publishing Co., Easton Pa. ("Remington's"). Therapeutically effective amounts of glucocorticoid blockers suitable for practice of the method of the invention will typically range from about 0.5 to about 35 milligrams per kilogram (mg/kg). A person of ordinary skill in the art will be able without undue experimentation, having regard to that skill and this disclosure, to determine a therapeutically effective amount of a particular glucocorticoid blocker compound for practice of this invention. For example, a particular glucocorticoid blocker may be more effective at higher or lower doses. By evaluating a patient using the methods described herein, a skilled practitioner will be able to determine whether a patient is responding to treatment and will know how to adjust the dosage levels accordingly.

In general, glucocorticoid blocker compounds may be administered as pharmaceutical compositions by any method known in the art for administering therapeutic drugs. Compositions may take the form of tablets, pills, capsules, semisolids, powders, sustained release formulations, solutions, suspensions, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, may be found in such standard references as Alfonso AR: Remington's Pharmaceutical Sciences, 17th ed., Mack Publishing Company, Easton Pa., 1985. Suitable liquid carriers, especially for injectable solutions, include water, aqueous saline solution, aqueous dextrose solution, and glycols.

Aqueous suspensions of the invention contain a GR antagonist in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a GR antagonist in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Glucocorticoid blocker pharmaceutical formulations can be prepared according to any method known to the art for the manufacture of pharmaceuticals. Such drugs can contain sweetening agents, flavoring agents, coloring agents and preserving agents. Any glucocorticoid blocker formulation can be admixtured with nontoxic pharmaceutically acceptable excipients which are suitable for manufacture.

In one aspect, glucocorticoid blocker compounds suitable for use in the practice of this invention can be administered orally. The amount of a compound of this invention in the composition may vary widely depending on the type of composition, size of a unit dosage, kind of excipients, and other factors well known to those of ordinary skill in the art. In general, the final composition may comprise from 0.000001 percent by weight (% w) to 10% w of the glucocorticoid blocker compounds, preferably 0.00001% w to 1% w, with the remainder being the excipient or excipients. For example, the GR antagonist mifepristone is given orally in tablet form, with dosages in the range of between about 0.5 and 35 mg/kg, in other embodiments, dosages may range between about 0.75 mg/kg and 15 mg/kg, or may be about 10 mg/kg.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient. Pharmaceutical preparations for oral use can be obtained through combination of glucocorticoid blocker compounds with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxypropylmethyl-cellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

In another aspect, the GR antagonists of this invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

In another aspect, the GR antagonists of this invention can be administered by in intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

In another aspect, the GR antagonists of the invention can also be delivered transdermally, by a topical route, formulated as applicator sticks, solutions, suspensions, emulsions, gels, creams, ointments, pastes, jellies, paints, powders, and aerosols.

In still another aspect, the GR antagonists of the invention can also be delivered as microspheres for slow release in the body. For example, microspheres can be administered via intradermal injection of drug (e.g., mifepristone)-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The GR antagonist pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5, that is combined with buffer prior to use.

In one embodiment, the GR antagonist formulations of the invention are useful for parenteral administration, such as intravenous (IV) administration. The formulations for administration will commonly comprise a solution of the GR antagonist (e.g., mifepristone) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of GR antagonist in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the GR antagonist formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR antagonist into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

B. Determining Dosing Regimens for Glucocorticoid Receptor Antagonists

The methods of this invention treat gastroesophageal reflux disease in a subject. The amount of GR antagonist adequate to accomplish this is defined as a "therapeutically effective dose". The dosage schedule and amounts effective for this use, i.e., the "dosing regimen," will depend upon a variety of factors, including the severity of the gastroesophageal reflux disease, whether the treatment is being given during the course of a gastroesophageal reflux disease attack, or prophylactically, the patient's physical status, age, gastroesophageal reflux disease history, and the like. In calculating the dosage regimen for a patient, the mode of administration also is taken into consideration.

The dosage regimen also takes into consideration pharmacokinetics parameters well known in the art, i.e., the GR antagonists' rate of absorption, bioavailability, metabolism, clearance, and the like (see, e.g., Hidalgo-Aragones, J. Steroid Biochem. Mol. Biol. 58:611-617, 1996; Groning, Pharmazie 51:337-341, 1996; Fotherby, Contraception 54:59-69, 1996; Johnson, J. Pharm. Sci. 84:1144-1146, 1995; Rohatagi, Pharmazie 50:610-613, 1995; Brophy, Eur. J. Clin. Pharmacol. 24:103-108, 1983; the latest Remington's, supra). For example, in one study, less than 0.5% of the daily dose of mifepristone was excreted in the urine; the drug bound extensively to circulating albumin (see Kawai, supra, 1989). The state of the art allows the clinician to determine the dosage regimen for each individual patient, GR antagonist and disease or condition treated. As an illustrative example, the guidelines provided below for mifepristone can be used as guidance to determine the dosage regiment, i.e., dose schedule and dosage levels, of any GR antagonist administered when practicing the methods of the invention.

Single or multiple administrations of GR antagonist formulations can be administered depending on the dosage and frequency as required and tolerated by the patient. The formulations should provide a sufficient quantity of active agent, i.e., mifepristone, to effectively treat gastroesophageal reflux disease in a subject. Thus, one typical pharmaceutical formulations for oral administration of mifepristone is in a daily amount of between about 0.5 to about 35 mg per kilogram of body weight per day. In an alternative embodiment, dosages are from about 5 mg to about 15 mg per kg of body weight per patient per day are used in the practice of the invention. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable GR antagonist formulations will be known or apparent to those skilled in the art and are described in more detail in such publications as Remington's, supra. See also Nieman, In "Receptor Mediated Antisteroid Action," Agarwal, et al., eds., De Gruyter, New York, 1987.

After a pharmaceutical comprising a GR antagonist of the invention has been formulated in a acceptable carrier, it can be placed in an appropriate container and labeled for treatment of an indicated condition. For administration of GR antagonists, such labeling would include, e.g., instructions concerning the amount, frequency and method of administration. In one embodiment, the invention provides for a kit for treating gastroesophageal reflux disease in a subject which includes a GR antagonist and instructional material teaching the indications, dosage and schedule of administration of the GR antagonist.

It is understood that the examples and embodiments described herein are for illustrative purposes only and that various modifications or changes in light thereof will be suggested to persons skilled in the art and are to be included within the spirit and purview of this application and scope of the appended claims.

All publications and patent applications cited in this specification are herein incorporated by reference as if each individual publication or patent application were specifically and individually indicated to be incorporated by reference.

EXAMPLES

The following examples are offered to illustrate, but not to limit the claimed invention.

Example 1

Treating Gastroesophageal Reflux Disease Prophylactically Using Mifepristone

A person presents with gastroesophageal reflux disease presents with symptoms comprising heartburn that has a sub-sternal locus. The heartburn typically occurs after meals and often worsens when the patient is lying down. The patient is diagnosed with GERD. However, to confirm the diagnosis the patient is treated with Prilosec to suppress stomach acid secretion. The treatment with Prilosec inhibits the symptoms or GERD, confirming diagnosis.

To treat the GERD, administration of the glucocorticoid receptor (GR) antagonist, mifepristone (available from commercial sources such as Shanghai HuaLian Pharmaceuticals Co., Ltd., Shanghai, China), is initiated.

The subject is instructed to take a dosage of 600 mg daily, and to continue the mifepristone daily for six months. Dosages will be adjusted if necessary and further evaluations will be performed periodically throughout treatment.

Assessing Symptom Reduction and/or Prevention:

To delineate and assess the effectiveness of mifepristone in treating the subject's gastroesophageal reflux disease, the severity of gastroesophageal reflux symptoms is recorded and measured, and the healing of the esophageal tissues is monitored by endoscopy at baseline, 3 months, and 6 months.

Example 2

Measuring Cortisol Levels

To measure cortisol level in the subject of Example 1, afternoon Cortisol Test measurements are taken and used as the baseline cortisol measure. Cortisol levels are taken at Day 0, at two weeks after receiving the medication (Day 14), and each visit for up to six months and periodically thereafter.

The "Double Antibody Cortisol Kit" (Diagnostic Products Corporation, Los Angeles, Calif.) is used to measure blood cortisol levels. This test is a competitive radioimmunoassay in which $^{125}$I-labeled cortisol competes with cortisol from an clinical sample for antibody sites, and is performed essentially according to manufacturer's instructions using reagents supplied by manufacturer. Briefly, blood is collected by venipuncture and serum separated from the cells. The samples are stored at 2 to 8° C. for up to seven days, or up to two month frozen at −20° C. Before the assay, samples are allowed to come up to room temperature (15-28° C.) by gentle swirling or inversion. Sixteen tubes in duplicate at 25 microliters of serum per tube are prepared. Cortisol concentrations are calculated from the prepared calibration tubes. Net counts equal the average CPM minus the average non-specific CPM. Cortisol concentrations for the unknowns are estimated by interpolation from the calibration curve (Dudley et al., Clin. Chem. 31: 1264-1271, 1985).

It is understood that the examples and embodiments described herein are for illustrative purposes only and that various modifications or changes in light thereof will be suggested to persons skilled in the art and are to be included within the spirit and purview of this application and scope of the claims.

What is claimed is:

1. A method of treating gastroesophageal reflux disease in a subject in need thereof; the method comprising the step of administering to the subject an effective amount of a specific glucocorticoid receptor antagonist to treat gastroesophageal reflux disease in the subject, with the proviso that the subject is not otherwise in need of treatment with a glucocorticoid receptor antagonist.

2. The method of claim 1, wherein the subject is a human.

3. The method of claim 1, wherein the treatment for gastroesophageal reflux disease is administered during the course of an attack of gastroesophageal reflux disease.

4. The method of claim 1, wherein the glucacorticoid receptor antagonist comprises a steroidal skeleton with at least one phenyl-containing moiety in the 11-beta position of the steroidal skeleton.

5. The method of claim 4, wherein the phenyl-containing moiety in the 11-beta position of the steroidal skeleton is a dimethylaminophenyl moiety.

6. The method of claim 5, wherein the glucocorticoid receptor antagonist is mifepristone.

7. The method of claim 5, wherein the glucocorticoid receptor antagonist is selected from the group consisting of 11β-(4-dimethylaminoethoxyphenyl)-17α-propynyl-17β-hydroxy-4,9-estradien-3-one and 17β-hydroxy-17α-19-(4-methylphenyl)androsta-4,9(11)-dien-3-one.

8. The method of claim 1, wherein the glucocorticoid receptor antagonist is selected from the group consisting 4α(S)-Benzyl-2(R)-prop-1-ynyl-1,2,3,4,4α,9,10,10α(R)-octahydro-phenanthrene-2,7-diol and 4α(S)-Benzyl-2(R)-chloroethynyl-1,2,3,4,4α,9,10,10α(R)-octahydro-phenanthrene-2,7-diol.

9. The method of claim 1, wherein the glucocorticoid receptor antagonist is (11β,17β)-11-(1,3-benzodioxol-5-yl)-17-hydroxy-17-(1-propynyl)estra-4,9-dien-3-one.

10. The method of claim 1, wherein the glucocorticoid receptor antagonist is administered in an amount of between about 0.5 to about 35 mg per kilogram of body weight per day.

11. The method of claim 10, wherein the glucocorticoid receptor antagonist is administered in an amount of between about 5 to about 15 mg per kilogram of body weight per day.

12. The method of claim 1, wherein the administration is once per day.

13. The method of claim 1, wherein the mode of administration is by a transdermal application, by a nebulized suspension, or by an aerosol spray.

14. The method of claim 1, wherein the mode of administration is oral.

* * * * *